United States Patent
Sinha et al.

(10) Patent No.: US 7,977,380 B2
(45) Date of Patent: *Jul. 12, 2011

(54) INHIBITORS OF PLASMA KALLIKREIN

(75) Inventors: Sukanto Sinha, San Francisco, CA (US); Tamie Jo Chilcote, San Francisco, CA (US)

(73) Assignee: Activesite Pharmaceticals, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/623,326

(22) Filed: Nov. 20, 2009

(65) Prior Publication Data

US 2010/0130563 A1 May 27, 2010

Related U.S. Application Data

(63) Continuation of application No. 11/830,539, filed on Jul. 30, 2007, now Pat. No. 7,625,944.

(60) Provisional application No. 60/919,031, filed on Mar. 20, 2007, provisional application No. 60/834,377, filed on Jul. 31, 2006.

(51) Int. Cl.
| | |
|---|---|
| *A61K 31/4436* | (2006.01) |
| *A61K 31/4439* | (2006.01) |
| *A61K 31/426* | (2006.01) |
| *A61K 31/4192* | (2006.01) |
| *A61K 31/415* | (2006.01) |
| *A61K 31/381* | (2006.01) |
| *A61K 31/343* | (2006.01) |
| *A61K 31/341* | (2006.01) |
| *A61K 31/404* | (2006.01) |

(52) U.S. Cl. ........ 514/469; 514/443; 514/419; 514/471; 514/448; 514/423; 514/406; 514/365; 514/343; 514/336

(58) Field of Classification Search ............ 514/469, 514/443, 419, 471, 448, 423, 406, 365, 343, 514/336

See application file for complete search history.

(56) References Cited

U.S. PATENT DOCUMENTS

| | | | |
|---|---|---|---|
| 5,998,424 A | 12/1999 | Galemmo, Jr. et al. | |
| 6,337,344 B1 | 1/2002 | Defossa et al. | |
| 7,625,944 B2 * | 12/2009 | Sinha et al. | ............. 514/469 |

FOREIGN PATENT DOCUMENTS

WO  WO 2008/016883 A2  2/2008

OTHER PUBLICATIONS

International Search Report mailed on Feb. 6, 2008, for PCT Application No. PCT/US07/74761 filed on Jul. 30, 2007, 3 pages.

* cited by examiner

*Primary Examiner* — Jason M Nolan
(74) *Attorney, Agent, or Firm* — Kilpatrick Townsend & Stockton LLP

(57) ABSTRACT

The present invention provides compounds that inhibit the activity of plasma kallikrein (PK) and methods of preventing and treating the formation of thrombin during or after a PK dependent disease or condition, for example, after fibrinolysis treatment.

7 Claims, 6 Drawing Sheets

INHIBITORS OF PLASMA KALLIKREIN

CROSS-REFERENCES TO RELATED APPLICATIONS

This application claims the priority to U.S. Provisional Patent Application No. 60/919,031, filed Mar. 20, 2007 and U.S. Provisional Patent Application No. 60/834,377, filed Jul. 31, 2006, which are hereby incorporated by reference in their entirety for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Thrombus formation is essential for preventing blood loss and allowing repair of an injured vessel, a process known as hemostasis, yet a thrombus can also be pathologic when it occludes a blood vessel depriving tissue of oxygen. The occlusion of an artery by a thrombus, arterial thrombosis, most often occurs at the site of a ruptured or eroded atherosclerotic plaque (Kou, V. et al., (2006) *Mt. Sinai J. Med.* 73: 449-468). Specific occlusion of the coronary arteries results in acute coronary syndrome which includes unstable angina and myocardial infarction (MI).

A fibrin clot may be produced in blood by initiation of one of two distinct routes, the intrinsic and extrinsic pathways, which converge onto a common pathway of coagulation (Macfarlane, R. G. (1964) *Nature* 202: 498-9; Davie, E. W. et al. (1964) *Science* 145: 1310-12; Joseph, K. et al. (2005) *Advances Immunology* 86: 159-208). Experimental data have suggested both PK- and FXII-deficient individuals have severely impaired intrinsic pathway-mediated clot formation despite their lack of bleeding phenotype (Ratnoff, O. D. et al. (1955) *J. Clin. Invest.* 34: 602-613; Colman, R. W. (2001) *In Hemostasis and Thrombosis: Basic principles and clinical practice.* R. W. Colman et al eds. Lippincott Williams & Wilkins, Philadelphia, Pa. 103-122; Rosen, E. D. et al. (1997) *Nature* 390: 290-294; Hathaway, W. E., et al. (1965) *Blood* 26: 521-32; Lawrie, A. S. et al (1998) *Clin. Lab. Haematol.* 20: 179-86; and Bates, et al., (2005) *Circulation* 112: 53-60). In the intrinsic pathway, by binding to the surface, a small amount of factor XII (FXII) is activated (FXIIa) which in turn activates plasma kallikrein (PK) through proteolysis. Importantly, PK then generates additional FXIIa in a feedback loop which in turn activates factor XI (FXI) to FXIa to connect to the common pathway. Although the initial activation of the intrinsic pathway is through a small amount of FXIIa activating a small amount of PK, it is the subsequent feedback activation of FXII by PK that controls the extent of activation of the intrinsic pathway and hence downstream coagulation (Hathaway, W. E., et al. (1965) *Blood* 26: 521-32).

Current treatment for acute MI or ischemic stroke in a hospital setting requires emergency measures to dissolve the occluding thrombus and allow reperfusion (restored blood flow). One of the common ways of doing this is by treating the patients with fibrinolytic agents, such as tissue plasminogen activator (t-PA) or streptokinase, agents that lead to the generation of active plasmin from plasminogen. Plasmin cleaves the fibrin meshwork of the thrombus, therefore leading to clot dissolution. Such fibrinolytic agents are the most frequently used treatment for reperfusion worldwide. However, fibrinolysis is also associated with a high degree of re-thrombosis with subsequent rates of reocclusion of up to 50% depending on the study (Zijlstra, F. et al (1993) *N. Engl. J. Med.* 328: 680-4; Brodie, B. R. et al. (1994) *Circulation* 90: 156-62; Stone, G. W. et al (1999) *Circulation* 99: 1548-54; Tamai, H. et al, MAJIC Investigators (2004) *Am. Heart J.* 147: E9; Verheugt, F. W. et al (1996) *J. Am. Coll. Cardiol.* 27: 766-73).

Patients who have undergone acute MI show clinical evidence of being in a hypercoagulable (clot-promoting) state. This hypercoagulability is paradoxically additionally aggravated in those receiving fibrinolytic therapy. Increased generation of thrombin, as measured by thrombin-antithrombin III (TAT) levels up to 2-fold higher, is observed in patients undergoing such treatment compared to the already high levels observed in those receiving heparin alone (Hoffmeister, H. M. et al (1998) *Circulation* 98: 2527-33). The increase in thrombin has been proposed to result from plasmin-mediated activation of the intrinsic pathway. Plasmin-mediated activation of the intrinsic pathway system is known to occur in blood (Ewald, G. A. et al. (1995) *Circulation* 91: 28-36), and it has been suggested that this occurs as a consequence of direct activation of FXII by plasmin.

Not only does the fibrinolysis-induced hypercoagulability lead to increased rates of reocclusion, it is also probably responsible, at least in part, for failure to achieve complete fibrinolysis of the clot, a major shortcoming of fibrinolytic therapy (Keeley, E. C. et al. (2003) *Lancet* 361: 13-20). Another problem in fibrinolytic therapy is the accompanying 3-fold elevated risk of intracranial hemorrhage (ICH) (Menon, V. et al (2004) 126: 549S-575S; Fibrinolytic Therapy Trialists' Collaborative Group (1994) *Lancet* 343: 311-322). Hence, an adjunctive anti-coagulant therapy that does not increase the risk of bleeding, but inhibits the formation of new thrombin, would be greatly beneficial.

It has been found that treatment of wild-type mice with an irreversible inhibitor of FXII led to fewer occluded vessels and less ischemic cortical damage and inhibition of FXII, would be protective for arterial thrombosis, such as that occurring during acute MI or during thrombotic stroke (WO/2006 066878 A1). However, peptidic drugs have numerous shortcomings including limited application to acute studies because of short half lives, i.v. administration requiring medical intervention, and the development of anti-peptide antibodies by patients undergoing treatment.

Therefore, there is a need to develop small molecule inhibitors of PK that will overcome these limitations. In particular, inhibitors that can push the balance of fibrinolysis/thrombosis at the occluding thrombus toward dissolution, promote reperfusion and also attenuate the hypercoagulability state, thus preventing the thrombus from reforming and reoccluding the vessel. The present invention fulfills this and other needs.

BRIEF SUMMARY OF THE INVENTION

In one aspect, the present invention provides a compound having the formula:

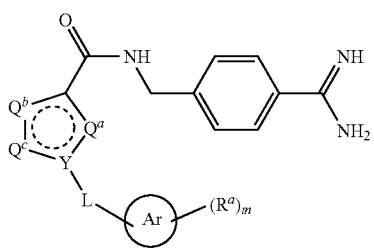

wherein Ar is a bond or an aromatic ring selected from the group consisting of benzene, pyridine and pyrimidine; the subscript m is an integer of from 0 to 5; each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —NR$^1$—OR$^1$, —N=C=O, —N=C=S, —Si(R$^1$)$_3$, —NH—NHR$^1$, —NHC(O)NHNH$_2$, NO, —N=C=NR$^1$ and —S—CN, wherein each R$^1$ is independently alkyl; L is a linking group selected from the group consisting of a bond, CH$_2$ and SO$_2$;

$Q^a$, $Q^b$, and $Q^c$ are each members independently selected from the group consisting of N, S, O and C(R$^q$) wherein each R$^q$ is independently selected from the group consisting of H, $C_{1-8}$ alkyl and phenyl, and the ring having $Q^a$, $Q^b$, $Q^c$ and Y as ring vertices is a five-membered ring having two double bonds; Y is a member selected from the group consisting of C and N; when Ar is a bond, m is 1; when Ar is an aromatic ring, m is an integer of from 0-5; and pharmaceutically acceptable salts thereof.

In another aspect, the present invention provides a compound having the formula:

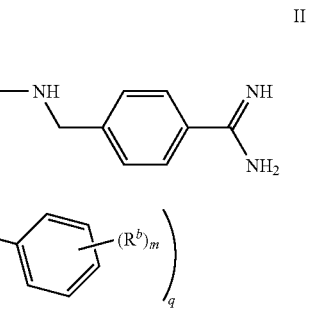

wherein the subscript m is an integer of from 0 to 5; the subscript n is an integer of from 0 to 4; the subscript q is an integer of from 0 to 1; L is a linking group selected from the group consisting of a bond, CH$_2$ and SO$_2$; each of R$^b$ and R$^c$ is independently selected from the group consisting of cycloalkyl, haloalkyl, halogen, —OH, —OR$^2$, —OSi(R$^2$)$_3$, —OC(O)O—R$^2$, —OC(O)R$^2$, —OC(O)NHR$^2$, —OC(O)N(R$^2$)$_2$, —SH, —SR$^2$, —S(O)R$^2$, —S(O)$_2$R$^2$, —SO$_2$NH$_2$, —S(O)$_2$NHR$^2$, —S(O)$_2$N(R$^2$)$_2$, —NHS(O)$_2$R$^2$, —NR$^2$S(O)$_2$R$^2$, —C(O)NH$_2$, —C(O)NHR$^2$, —C(O)N(R$^2$)$_2$, —C(O)R$^2$, —C(O)H, —C(=S)R$^2$, —NHC(O)R$^2$, —NR$^2$C(O)R$^2$, —NHC(O)NH$_2$, —NR$^2$C(O)NH$_2$, —NR$^2$C(O)NHR$^2$, —NHC(O)NHR$^2$, —NR$^2$C(O)N(R$^2$)$_2$, —NHC(O)N(R$^2$)$_2$, —CO$_2$H, —CO$_2$R$^2$, —NHCO$_2$R$^2$, —NR$^2$CO$_2$R$^2$, —R$^2$, —CN, —NO$_2$, —NH$_2$, —NHR$^2$, —N(R$^2$)$_2$, —NR$^2$S(O)NH$_2$, —NR$^2$S(O)$_2$NHR$^2$, —NH$_2$C(=NR$^2$)NH$_2$, —N=C(NH$_2$)NH$_2$, —C(=NR$^2$)NH$_2$, —NH—OH, —NR$^2$—OH, —NR$^2$—OR$^2$, —N=C=O, —N=C=S, —Si(R$^2$)$_3$, —NH—NHR$^2$, —NHC(O)NHNH$_2$, NO, —N=C=NR$^2$ and —S—CN, wherein each R$^2$ is independently alkyl; when q is 0, Z is a member selected from the group consisting of O, S and NR$^d$ wherein R$^d$ is H or $C_1$-$C_8$ alkyl; when q is 1, Z is N; and pharmaceutically acceptable salts thereof.

In yet another aspect, the present invention provides a pharmaceutical composition. The composition includes a compound of formula I or II, in combination with a pharmaceutically acceptable excipient.

In still another aspect, the present invention provides a method of treating thrombosis in a subject in need thereof. The method includes administering to the subject a compound of formula I or II or a PK specific monoclonal antibody.

In a further aspect, the present invention provides a method of treating a plasma kallikrein dependent disease or condition in a subject in need thereof. The method includes administering to the subject a compound of formula I or II or a PK-specific monoclonal antibody.

DETAILED DESCRIPTION OF THE INVENTION

I. Definitions

Figure 1:
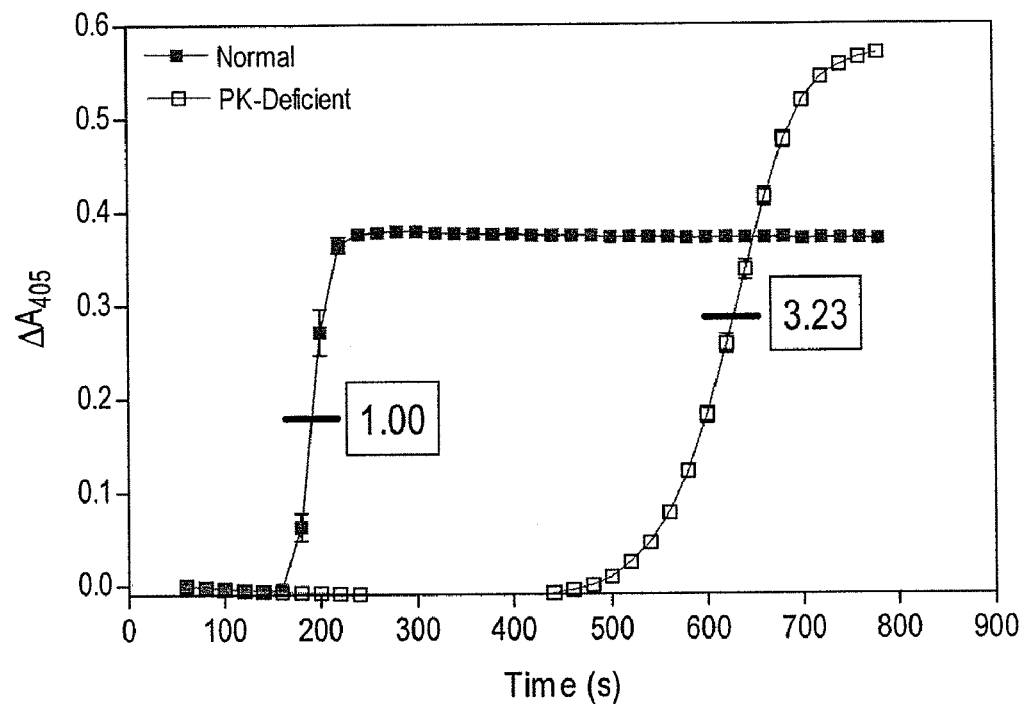
FIG. 1 illustrates a comparison of coagulation times of PK-deficient plasma with normal plasma following Actin FS addition.

Unless otherwise stated the following terms used in the specification and claims have the meanings given below.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2]octane, etc. When a prefix is not included to indicate the number of ring carbon atoms in a cycloalkyl, the radical or portion thereof will have 8 or fewer ring carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means a monovalent monocyclic, bicyclic or polycyclic aromatic hydrocarbon radical of 5 to 14 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl cut, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one to five heteroatoms or heteroatom functional groups have replaced a ring carbon, while retaining aromatic properties, e.g., pyridyl, quinolinyl, quinazolinyl, thienyl, and the like. The heteroatoms are selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriaziniyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

Substituents for the aryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —$N_3$, perfluoro($C_1$-$C_4$) alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts. The term "pharmaceutically acceptable" is meant the carrier, diluent or excipient must be compatible with the other ingredients of the formulation and not deleterious to the recipient thereof.

The term "composition" as used herein is intended to encompass a product comprising the specified ingredients in the specified amounts, as well as any product which results, directly or indirectly, from combination of the specified ingredients in the specified amounts.

The term "subject" as used herein is meant to include animals, such as mammals, including, but are not limited to, primates (e.g. humans), cows, sheeps, goats, horses, dogs, cats, rabbits, rats, mice and the like.

II. General

The present invention relates to compounds for inhibiting the activity of plasma kallikrein (PK) and methods of using the compounds and pharmaceutical compositions for the prevention and treatment of blood coagulation, such as thrombosis, and PK-dependent diseases and conditions. For example, the compounds inhibit the formation of thrombin by the intrinsic pathway and thus reduce the risk of new pathogenic thrombus formation (reocclusion) and also improve fibrinolytic-induced reperfusion when given as adjunctive therapy with a fibrinolytic regimen.

The present invention offers several advantages. First, high levels of inhibition of PK activity will not have any untoward effects, based on the lack of any observed phenotypes in PK-deficient individuals. Second, PK inhibition following acute myocardial infarction (MI), ischemic stroke or deep vein thrombosis (DVT) offers a powerful additional advantage over other anti-coagulants such as heparin (including LMWH) or direct thrombin and FXa inhibitors being clinically developed in that it will not affect normal hemostasis, thus not increasing the already elevated risk of bleeding in such patients. Third, by lowering the amount of thrombin that is concurrently generated upon fibrinolytic therapy, PK inhibitors improves the clinical course of reperfusion upon fibrinolytic treatment, resulting in more effective outcome for such treatment, and allow the application of a lower dose of fibrinolytic to obtain a therapeutic effect, while lowering the risk of ICH. Fourth, the compounds and methods of the present invention have stable and long half-lives for acute studies, low possibility of developing drug resistance from patients, and do not require other medical intervention.

III. Compounds

In one aspect, the present invention provides compounds having the formula:

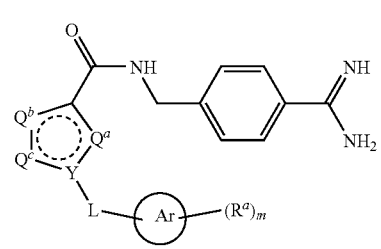

I

Ar is a bond or an aromatic ring selected from the group consisting of benzene, pyridine and pyrimidine. When Ar is a bond, m is 1. When Ar is an aromatic ring, m is an integer from 0-5. In one embodiment, Ar is benzene or pyridine. In another embodiment, Ar is a bond.

The subscript m is an integer from 0 to 5. In one embodiment, m is 0.

Each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —N=C=O, —N=C=S, —Si(R$^1$)$_3$, —NH—NHR$^1$, —NHC(O)NHNH$_2$, NO, —N=C=NR$^1$ and —S—CN, wherein each R$^1$ is independently alkyl. In one embodiment, R$^1$ is C$_1$-C$_8$ alkyl. In another embodiment, R$^1$ is unsubstituted aryl, such as phenyl or pyridyl, or a substituted aryl, such as a substituted phenyl or a substituted pyridyl.

In one embodiment, each $R^a$ is independently selected from the group consisting of C$_1$-C$_8$ alkyl, C$_1$-C$_8$ alkoxy, aryl, aryl(C$_1$-C$_8$ alkyl), halogen, —NH$_2$, —NH(C$_1$-C$_8$ alkyl), —N(C$_1$-C$_8$ alkyl)$_2$, —CN, —C(=O)(C$_1$-C$_8$ alkyl), —(C=O)NH$_2$, —(C=O)NH(C$_1$-C$_8$ alkyl), —C(=O)N(C$_1$-C$_8$ alkyl)$_2$, —OH, —COOH, —COO(C$_1$-C$_8$ alkyl), —OCO(C$_1$-C$_8$ alkyl), —O(C=O)O(C$_1$-C$_8$ alkyl), —NO$_2$, —SH, —S(C$_1$-C$_8$ alkyl), —NH(C=O)(C$_1$-C$_8$ alkyl), —NH(C=O)O(C$_1$-C$_8$ alkyl), —O(C=O)NH(C$_1$-C$_8$ alkyl), —SO$_2$(C$_1$-C$_8$ alkyl), —NHSO$_2$(C$_1$-C$_8$ alkyl) and —SO$_2$NH(C$_1$-C$_8$ alkyl). In another embodiment, each $R^a$ is independently selected from the group consisting of C$_1$-C$_8$ alkyl, C$_1$-C$_8$ alkoxy, phenyl, phenyl(C$_1$-C$_8$ alkyl), halogen, —CN, —NH$_2$, —NH(C$_1$-C$_8$ alkyl), —N(C$_1$-C$_8$ alkyl)$_2$, —(C=O)CH$_3$, —(C=O)NH$_2$, —OH, —COOH, —COO(C$_1$-C$_8$ alkyl), —OCO(C$_1$-C$_8$ alkyl), —O(C=O)O(C$_1$-C$_8$ alkyl), —NO$_2$, —SH, —S(C$_1$-C$_8$ alkyl), and —NH(C=O)(C$_1$-C$_8$ alkyl). In yet another embodiment, each $R^a$ is independently selected from the group consisting of C$_1$-C$_8$ alkyl, C$_1$-C$_8$ alkoxy, phenyl, phenyl(C$_1$-C$_8$ alkyl), phenoxy, aryloxy, halogen, —CN, —NH$_2$, —NH-aryl, —(C=O)CH$_3$, —(C=O)NH$_2$, —OH, —COOH, —COO($C_1$-$C_8$ alkyl), —OCO($C_1$-$C_8$ alkyl), —COO-aryl, —OC(O)-aryl, —O(C═O)O($C_1$-$C_8$ alkyl)-$NO_2$, —SH, —S($C_1$-$C_8$ alkyl), —NH(C═O)($C_1$-$C_8$ alkyl) and the like. For example, $R^a$ is halogen, such as Cl, Br or I.

L is a linking group selected from the group consisting of a bond, $CH_2$ and $SO_2$.

$Q^a$, $Q^b$, and $Q^c$ are each members independently selected from the group consisting of N, S, O and C($R^q$) wherein each $R^q$ is independently selected from the group consisting of H, $C_{1-8}$ alkyl, halogen and phenyl, and the ring having $Q^a$, $Q^b$, $Q^c$ and Y as ring vertices is a five-membered ring having two double bonds.

In a first group of embodiments, $Q^a$ is N and $Q^b$ and $Q^c$ are each selected from N, O and C($R^q$). In certain instances, $Q^a$ is N and $Q^c$ and $Q^b$ are each independently selected from N and C($R^q$). In certain other instances, $Q^a$ is N and $Q^c$ and $Q^b$ are each selected from C($R^q$) and O. In yet certain other instances, $Q^a$ is N, $Q^c$ is a member selected from N and O, and $Q^b$ is the other member selected from N and O.

In a second group of embodiments, $Q^a$ is O and $Q^b$ and $Q^c$ are each selected from N, O and C($R^q$). In certain instances, $Q^a$ is O and $Q^c$ and $Q^b$ are each independently selected from N and C($R^q$).

In a third group of embodiments, $Q^a$ is C($R^q$) and $Q^b$ and $Q^c$ are each selected from N, O and C($R^q$). In certain instances, $Q^a$ is C($R^q$) and $Q^b$ and $Q^c$ are each independently selected from N and O. In certain other instances, $Q^a$ is C($R^q$) and $Q^b$ and $Q^c$ are each independently selected from N and C($R^q$). In yet certain other instances, $Q^a$ is C($R^q$) and $Q^b$ and $Q^c$ are each independently selected from O and C($R^q$). In one occurrence, $Q^a$ is C($R^q$), $Q^b$ is O and $Q^c$ is (C$R^q$).

Y is a member selected from the group consisting of C and N. In one embodiment, Y is C, $Q^a$ is S and Ar is selected from phenyl or pyridyl. In another embodiment, Y is N, $Q^a$, $Q^b$ and $Q^c$ are each independently C($R^q$), wherein $R^q$ is H or $C_{1-8}$alkyl. In one instance, Y is N, $Q^a$ and $Q^c$ are C($R^q$) and $Q^b$ is CH. In a preferred embodiment, Y is N.

In one embodiment, L is a bond, Y is N. In another embodiment, L is a bond, Y is N and Ar is a benzene ring. In yet another embodiment, L is $CH_2$ and Y is N. In still another embodiment, L is a bond and Y is C. In a further embodiment, L is $SO_2$ and Y is N.

In a preferred embodiment, $Q^a$, $Q^b$ and $Q^c$ are each independently C$R^q$. In another preferred embodiment, L is a bond or $CH_2$. In still another preferred embodiment, Ar is benzene. In still another preferred embodiment, $R^a$ is —H and $C_1$-$C_8$ alkyl.

In one embodiment, the present invention provides compounds of formula I having a formula set forth in Table 1 below:

TABLE 1

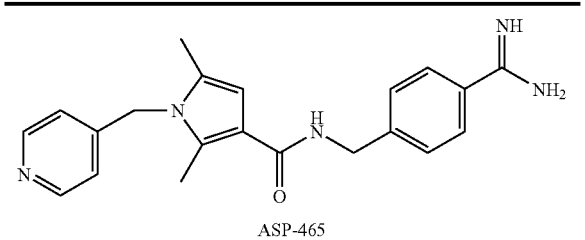

ASP-465

TABLE 1-continued

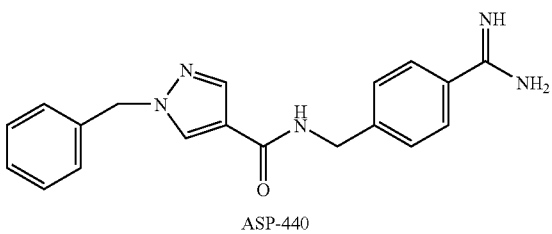

ASP-440

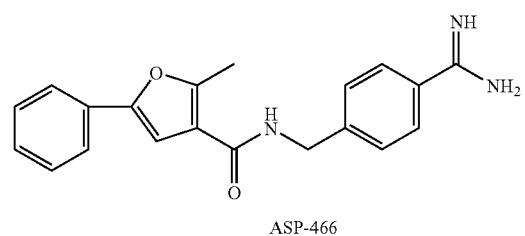

ASP-466

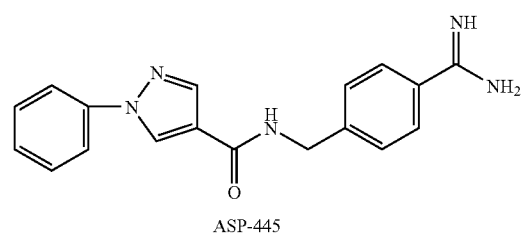

ASP-445

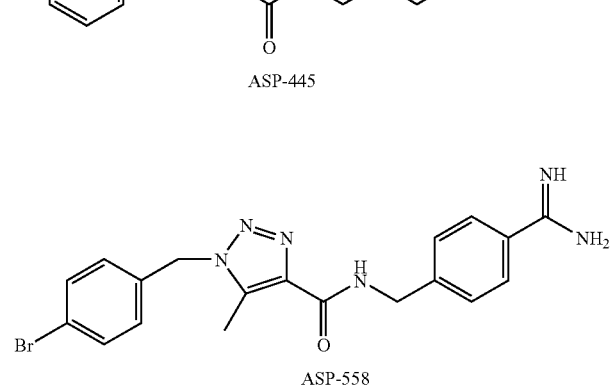

ASP-558

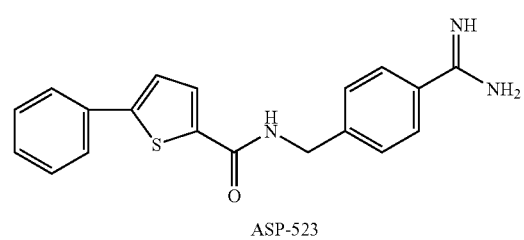

ASP-523

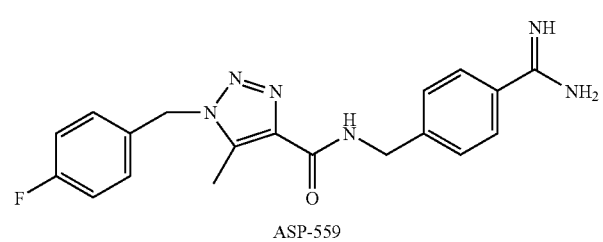

ASP-559

TABLE 1-continued
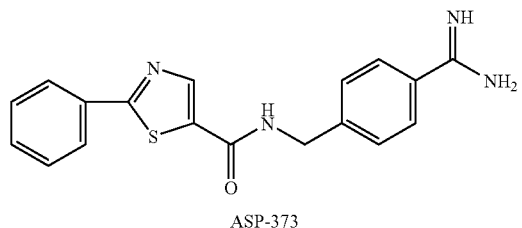
ASP-373
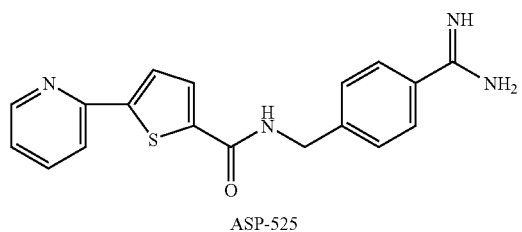
ASP-525
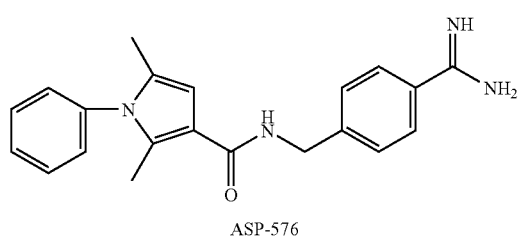
ASP-576
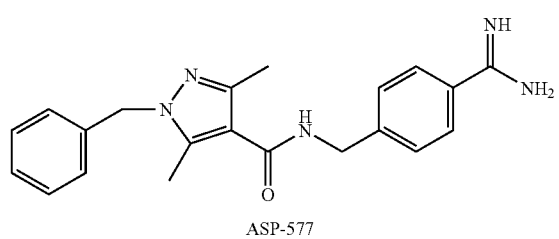
ASP-577
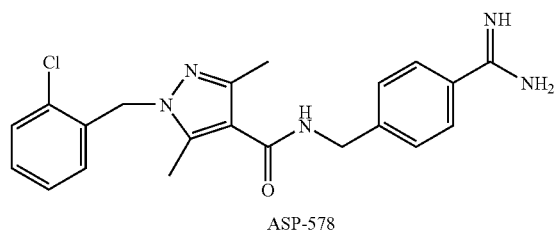
ASP-578
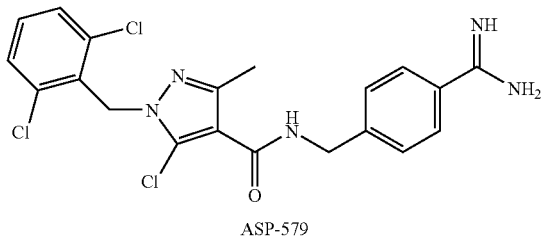
ASP-579
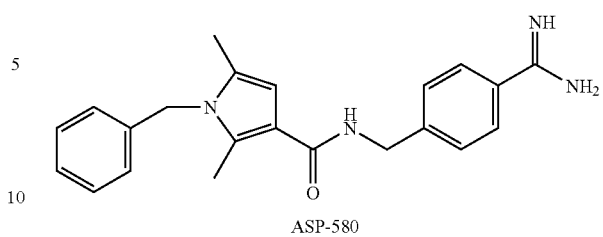
ASP-580
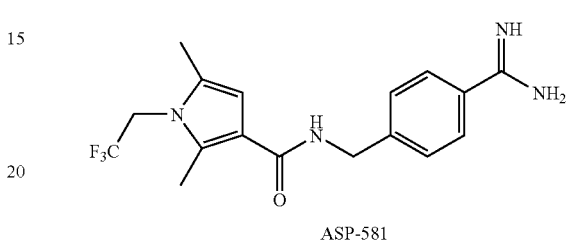
ASP-581
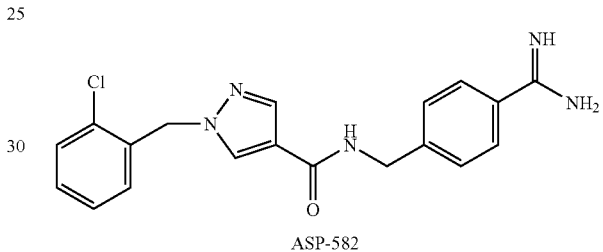
ASP-582
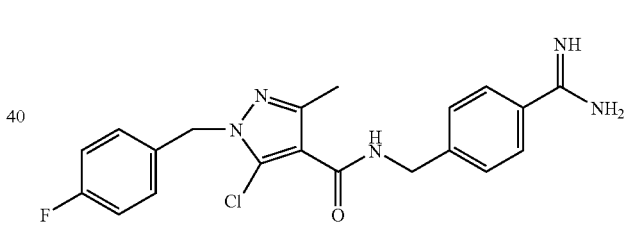
ASP-583
In another embodiment, the compounds of formula I have a subformula Ia:
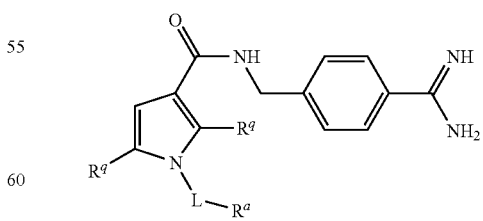
Ia
$R^q$ and L are as defined above. In one instance, $R^q$ is independently —H or $C_{1-8}$ alkyl and L is a bond or —$CH_2$—. In another instance, $R^a$ is halo-($C_1$-$C_8$ alkyl). For example, $R^a$ is —$CF_3$, $CH_2CF_3$.

In one embodiment, the compounds of formula I have a subformula Ib:

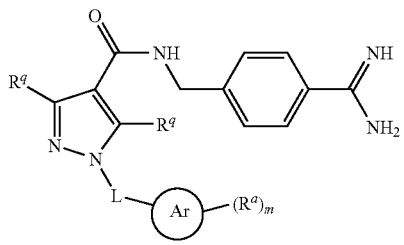

wherein Ar is an aromatic ring. In one instance, each $R^q$ is independently H, $C_1$-$C_8$ alkyl or halogen. In another instance, L is a bond or $CH_2$. In yet another instance, Ar is benzene. In still another instance, m is 0. In one occurrence, each $R^q$ is H, L is $CH_2$, Ar is benzene and m is 0. In another occurrence, each $R^q$ is H, L is a bond, Ar is benzene and m is 0.

In another aspect, the present invention provides compounds having the formula:

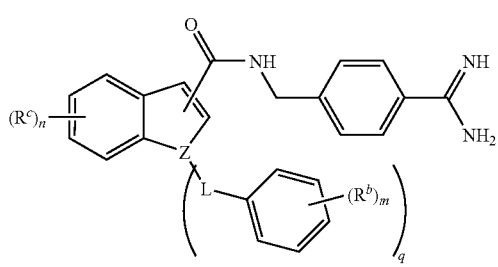

The subscript m is an integer of from 0 to 5. The subscript n is an integer of from 0 to 4. The subscript q is an integer of from 0 to 1. In one embodiment, the subscript m is 0. In another embodiment, the subscript n is an integer from 0 to 2. In yet another embodiment, the subscript q is 0. In still another embodiment, the subscript q is 1.

L is a linking group selected from the group consisting of a bond, $CH_2$ and $SO_2$. In one embodiment, L is $CH_2$ or $SO_2$.

Each of $R^b$ and $R^c$ is independently selected from the group consisting of cycloalkyl, haloalkyl, halogen, —OH, —$OR^2$, —$OSi(R^2)_3$, —$OC(O)O$—$R^2$, —$OC(O)R^2$, —$OC(O)NHR^2$, —$OC(O)N(R^2)_2$, —SH, —$SR^2$, —$S(O)R^2$, —$S(O)_2R^2$, —$SO_2NH_2$, —$S(O)_2NHR^2$, —$S(O)_2N(R^2)_2$, —$NHS(O)_2R^2$, —$NR^2S(O)_2R^2$, —$C(O)NH_2$, —$C(O)NHR^2$, —$C(O)N(R^2)_2$, —$C(O)R^2$, —C(O)H, —$C(=S)R^2$, —$NHC(O)R^2$, —$NR^2C(O)R^2$, —$NHC(O)NH_2$, —$NR^2C(O)NH_2$, —$NR^2C(O)NHR^2$, —$NHC(O)NHR^2$, —$NR^2C(O)N(R^2)_2$, —$NHC(O)N(R^2)_2$, —$CO_2H$, —$CO_2R^2$, —$NHCO_2R^2$, —$NR^2CO_2R^2$, —$R^2$, —CN, —$NO_2$, —$NH_2$, —$NHR^2$, —$N(R^2)_2$, —$NR^2S(O)NH_2$, —$NR^2S(O)_2NHR^2$, —$NH_2C(=NR^2)NH_2$, —$N=C(NH_2)NH_2$, —$C(=NR^2)NH_2$, —NH—OH, —$NR^2$—OH, —$NR^2$—$OR^2$, —N=C=O, —N=C=S, —$Si(R^2)_3$, —NH—$NHR^2$, —$NHC(O)NHNH_2$, NO, —N=C=$NR^2$ and —S—CN, wherein each $R^2$ is independently alkyl. In one embodiment, $R^2$ is $C_1$-$C_8$ alkyl. In another embodiment, $R^2$ is unsubstituted aryl, such as phenyl or pyridyl, or a substituted aryl, such as a substituted phenyl or a substituted pyridyl.

In one embodiment, each of $R^b$ and $R^c$ is independently selected from the group consisting of $C_1$-$C_8$ alkyl, $C_1$-$C_8$ alkoxy, aryl, aryl($C_1$-$C_8$ alkyl), halogen, —$NH_2$, —$NH(C_1$-$C_8$ alkyl), —$N(C_1$-$C_8$ alkyl)$_2$, —CN, —C(=O)($C_1$-$C_8$ alkyl), —(C=O)$NH_2$, —(C=O)NH($C_1$-$C_8$ alkyl), —C(=O)N($C_1$-$C_8$ alkyl)$_2$, —OH, —COOH, —COO($C_1$-$C_8$ alkyl), —OCO($C_1$-$C_8$ alkyl), —O(C=O)O($C_1$-$C_8$ alkyl)-$NO_2$, —SH, —S($C_1$-$C_8$ alkyl), —NH(C=O)($C_1$-$C_8$ alkyl), —NH(C=O)O($C_1$-$C_8$ alkyl), —O(C=O)NH($C_1$-$C_8$ alkyl), —$SO_2$($C_1$-$C_8$ alkyl), —$NHSO_2$($C_1$-$C_8$ alkyl) and —$SO_2NH$($C_1$-$C_8$ alkyl). In another embodiment, each $R^a$ is independently selected from the group consisting of $C_1$-$C_8$ alkyl, $C_1$-$C_8$ alkoxy, phenyl, phenyl($C_1$-$C_8$ alkyl), halogen, —CN, —$NH_2$, —$NH(C_1$-$C_8$ alkyl), —$N(C_1$-$C_8$ alkyl)$_2$, —(C=O)$CH_3$, —(C=O)$NH_2$, —OH, —COOH, —COO($C_1$-$C_8$ alkyl), —OCO($C_1$-$C_8$ alkyl), —O(C=O)O($C_1$-$C_8$ alkyl), —$NO_2$, —SH, —S($C_1$-$C_8$ alkyl), and —NH(C=O)($C_1$-$C_8$ alkyl). In yet another embodiment, each $R^a$ is independently selected from the group consisting of $C_1$-$C_8$ alkyl, $C_1$-$C_8$ alkoxy, phenyl, phenyl($C_1$-$C_8$ alkyl), phenoxy, aryloxy, halogen, —CN, —$NH_2$, —NH-aryl, —(C=O)$CH_3$, —(C=O)$NH_2$, —OH, —COOH, —COO($C_1$-$C_8$ alkyl), —OCO($C_1$-$C_8$ alkyl), —COO-aryl, —OC(O)-aryl, —O(C=O)O($C_1$-$C_8$ alkyl)-$NO_2$, —SH, —S($C_1$-$C_8$ alkyl), —NH(C=O)($C_1$-$C_8$ alkyl) and the like.

When q is 0, Z is a member selected from the group consisting of O, S and $NR^d$ wherein $R^d$ is H or $C_1$-$C_8$ alkyl. When q is 1, Z is N. In one embodiment, the subscript q is 0 and Z is selected from the group consisting of O, S and NH. In one instance, the subscript n is 0, 1 or 2. In one occurrence, Z is O or S. In another embodiment, the subscript q is 1. In one instance, L is $CH_2$ or $SO_2$.

In one embodiment, the present invention provides compounds of formula I having a formula set forth in Table 2 below:

TABLE 2

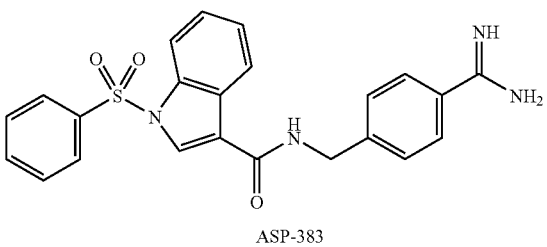

ASP-383

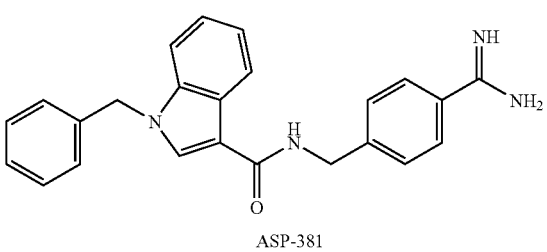

ASP-381

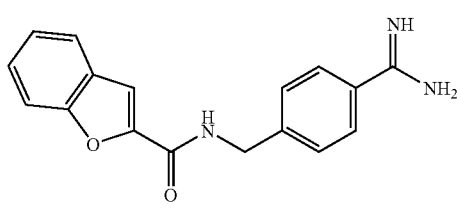

ASP-485

TABLE 2-continued

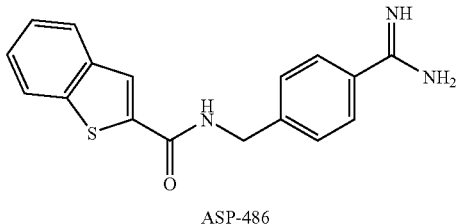

ASP-486

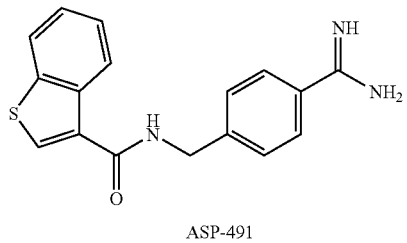

ASP-491

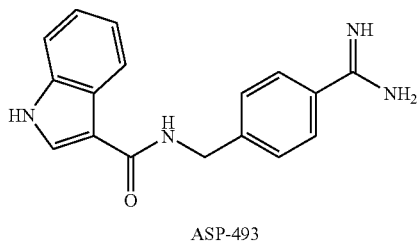

ASP-493

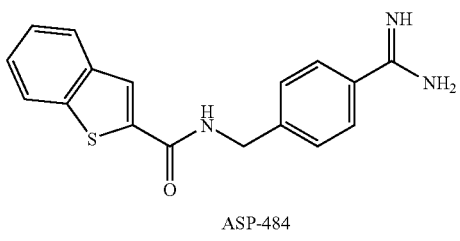

ASP-484

In one embodiment, the compounds of formula I have a subformula IIa:

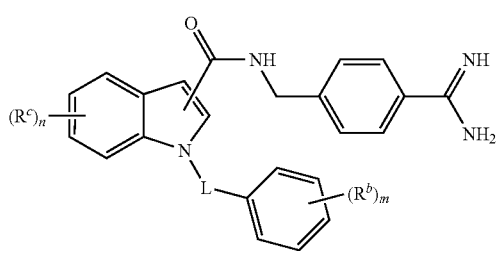

IIa

Substituents $R^b$ and $R^c$ and subscripts m are as defined above. In one instance, L is $CH_2$. In another instance, L is $SO_2$. In yet another instance, m is 0. In still another instance, n is 0.

In another embodiment, compounds of formula I have a subformula IIa-1:

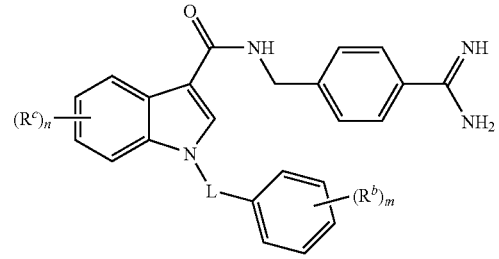

IIa-1

Table 3 provides compounds of PK inhibitors and their inhibition activities. The compound numbers correspond to numbers in Tables 1 and 2.

TABLE 3

| ASP- | Name | Calc MW | Exper. Mass (m + 1) | PK $K_{iapp}$ (μM) |
|---|---|---|---|---|
| 465 | 2,5-Dimethyl-1-pyridin-4-ylmethyl-1H-pyrrole-3-carboxylic acid 4-carbamimidoyl-benzylamide | 361.5 | 362.20 | 0.08 |
| 383 | 1-Benzenesulfonyl-1H-indole-3-carboxylic acid 4-carbamimidoyl-benzylamide | 432.5 | 433.10 | 0.17 |
| 381 | 1-Benzyl-1H-indole-3-carboxylic acid 4-carbamimidoyl-benzylamide | 382.5 | 383.20 | 0.24 |
| 440 | 1-Benzyl-1H-pyrazole-4-carboxylic acid 4-carbamimidoyl-benzylamide | 333.4 | 334.20 | 0.31 |
| 485 | Benzofuran-2-carboxylic acid 4-carbamimidoyl-benzylamide | 293.3 | | 0.87 |
| 466 | 2-Methyl-5-phenyl-furan-3-carboxylic acid 4-carbamimidoyl-benzylamide | 333.4 | 334.10 | 1.29 |
| 445 | 1-Phenyl-1H-pyrazole-4-carboxylic acid 4-carbamimidoyl-benzylamide | 319.4 | 320.10 | 1.43 |
| 486 | Benzo[b]thiophene-2-carboxylic acid 4-carbamimidoyl-benzylamide | 309.4 | | 1.57 |
| 491 | Benzo[b]thiophene-3-carboxylic acid 4-carbamimidoyl-benzylamide | 309.4 | | 2.11 |
| 493 | 1H-Indole-3-carboxylic acid 4-carbamimidoyl-benzylamide | 292.3 | | 2.45 |
| 484 | 1H-Indole-2-carboxylic acid 4-carbamimidoyl-benzylamide | 292.3 | | 2.52 |
| 558 | 1-(4-Bromo-benzyl)-5-methyl-1H-1,2,3-triazole-4-carboxylic acid 4-carbamimidoyl-benzylamide | 427.3 | 428.10 | 2.62 |
| 523 | 5-Phenyl-thiophene-2-carboxylic acid 4-carbamimidoyl-benzylamide | 335.4 | 336.10 | 7.66 |
| 559 | 1-(4-Fluoro-benzyl)-1H-1,2,3-triazole-4-carboxylic acid 4-carbamimidoyl-benzylamide | 352.4 | | 8.09 |
| 373 | 4-Methyl-2-phenyl-thiazole-5-carboxylic acid 4-carbamimidoyl-benzylamide | 350.4 | 351.10 | 8.87 |
| 525 | 5-Pyridin-2-yl-thiophene-2-carboxylic acid 4-carbamimidoyl-benzylamide | 336.4 | | 20.57 |
| 576 | 2,5-Dimethyl-1-phenyl-1H-pyrrole-3-carboxylic acid 4-carbamimidoyl-benzylamide | 346.4 | 347.1 | 0.04 |
| 577 | 1-Benzyl-3,5-dimethyl-1H-pyrazole-4-carboxylic acid 4-carbamimidoyl-benzylamide | 361.5 | 362.1 | 1.13 |
| 578 | 1-(2-Chloro-benzyl)-3,5-dimethyl-1H-pyrazole-4-carboxylic acid 4-carbamimidoyl-benzylamide | 395.9 | 396.1 | 1.64 |

TABLE 3-continued

| ASP- | Name | Calc MW | Exper. Mass (m + 1) | PK K$_{iapp}$ (μM) |
|---|---|---|---|---|
| 579 | 5-Chloro-1-(2,6-dichloro-benzyl)-3-methyl-1H-pyrazole-4-carboxylic acid 4-carbamimidoyl-benzylamide | 450.8 | 450.0 | 1.19 |
| 580 | 1-Benzyl-2,5-dimethyl-1H-pyrrole-3-carboxylic acid 4-carbamimidoyl-benzylamide | 360.5 | 361.1 | 0.03 |
| 581 | 2,5-Dimethyl-1-(2,2,2-trifluoro-ethyl)-1H-pyrrole-3-carboxylic acid 4-carbamimidoyl-benzylamide | 352.4 | 353.1 | 0.41 |
| 582 | 1-(2-Chloro-benzyl)-1H-pyrazole-4-carboxylic acid 4-carbamimidoyl-benzylamide | 367.8 | 368.0 | 0.47 |
| 583 | 5-Chloro-1-(4-fluoro-benzyl)-3-methyl-1H-pyrazole-4-carboxylic acid 4-carbamimidoyl-benzylamide | 399.9 | 400.0 | 2.38 |

Preparation of Compounds

As shown in the examples below, there are various synthetic routes by which a skilled artisan can prepare compounds and intermediates of the present invention. The scheme below provides a synthetic route that can be followed to access certain compounds of the present invention. Other routes or modification of the route shown would be readily apparent to a skilled artisan and within the scope of the present invention.

Scheme 1 shows one synthetic approach to the PK-inhibitors of the present invention.

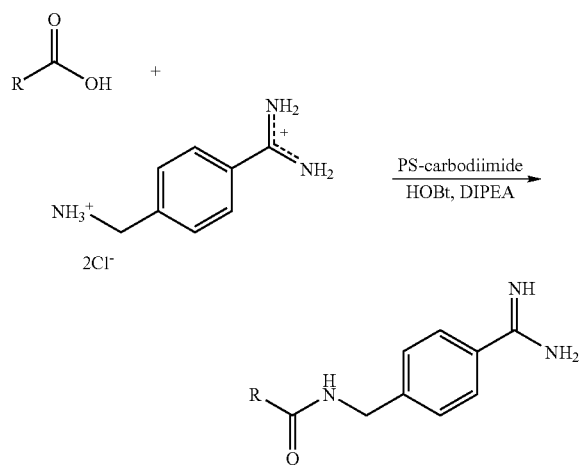

Scheme 1

In Scheme 1, carboxylic acids having various R groups are reacted with amidinobenzylamine in the presence of carbodiimide, HOBt and DIPEA to form carboxylic acid 4-carbamimidoyl-benzylamide derivatives. Amidinobenzylamine was purchased from Astatech, Bristol, Pa. The choice of a particular reaction condition is within the abilities of those of skill in the art.

IV. Pharmaceutical Compositions

In addition to having compounds of formula I and II provided above, the composition for prevention and treatment of thrombosis in humans and animals typically contain a pharmaceutical carrier, excipient and diluent.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable copolymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Thrombosis and PK-Dependent Conditions and Diseases

In yet another aspect, the present invention provides a method of treating thrombosis in a subject in need thereof. In one embodiment, the method includes inhibiting the activity of PK by contacting PK enzyme with a compound of formulas I or II. In another embodiment, the method includes administering to the subject a compound of formulas I or II. The subject can be a human or a mammal. In yet another embodiment, the method includes administering to the subject a therapeutically effective amount of compounds of formulas I or II. In one embodiment, the administering is conducted to a patient in post-myocardial infarction (MI) or post-ischemic stroke clinical setting. In one instance, the method includes administering a PK inhibitor following treatment with fibrinolytic agents.

Since PK activity is required for efficient FXII activation, individuals completely deficient of PK exhibit impaired coagulation in vitro via intrinsic pathway. In one embodiment, the compounds of the present invention are inhibitors of PK that can be used to inhibit the activity of PK. In another embodiment, an anti-PK monoclonal antibody (MAB), such as MAB 13G11, is used to inhibit the coagulation via the intrinsic pathway. In general, such methods comprise the step of contacting an PK with a sufficient yet effective amount of one or more PK inhibitors or PK-specific MAB as provided herein, in the presence of PK enzyme in aqueous solution and under conditions otherwise suitable for binding of the ligand to PK. The PK may be present in suspension (e.g., in an isolated membrane or cell preparation), or in a cultured or isolated cell.

Preferably, the amount of PK inhibitor contacted with the enzyme should be sufficient to inhibit PK activity in vitro as measured, for example, using colorimetric or fluorometric substrate cleavage assay.

In still another aspect, the present invention provides a method of treating a PK-dependent disease or condition in a subject in need thereof. The method includes administering to the subject a compound of formula I or II.

In a further aspect, the present invention provides a method of treating thrombosis in a subject in need thereof. The method includes administering to the subject a plasma kallikrein specific monoclonal antibody (MAB), for example, MAB 13G11.

Conditions That Can be Treated by PK Inhibitors:

The present invention provides inhibitors that inhibit the formation of thrombin by the intrinsic pathway and thus reduce the risk of new pathogenic thrombus formation (reocclusion) and also improve fibrinolytic-induced reperfusion when given as adjunctive therapy with a fibrinolytic regimen. Disease states that can be treated using the compounds of the present invention include, but are not limited to, ischemic stroke, stroke, inflammation, pain, acute myocardial infarction (MI), deep vein thrombosis (DVT), coagulations from post fibrinolytic treatment conditions (tissue plasminogen activator, streptokinase), angina, angioedema, sepsis, arthritis, blood loss during cardiopulmonary bypass, inflammatory bowel disease, diabetes and its complications and retinopathy.

For example, in patients with angioedema conditions, small polypeptide PK inhibitor (DX-88) (ecallantide) alleviates edema in patients with HAE. (see, Williams, A. et al. (2003) Transfus. Apher. Sci. 29: 255-258; Schneider, L. et al. Immunol. Jun. 6, 2007 [epub ahead of print]; and Levy, J. H. et al. (2006) Expert Opin. Invest. Drugs 15: 1077-1090). A bradykinin B2 receptor antagonist, Icatibant, is also effective in treating HAE (see, Bork, K. et al. (2007) J. Allergy Clin. Immunol. 119: 1497-1503). PK generates bradykinin, therefore inhibition of PK would inhibit bradykinin production.

For example, in coagulation resulting from fibrinolytic treatment (e.g. tissue plasminogen activator, streptokinase), higher levels of PK are found in patients undergoing fibrinolysis (see, Hoffmeister, H. M. et al. (1998) J. Cardiovasc. Pharmacol. 31: 764-72). Plasmin-mediated activation of the intrinsic pathway has been shown to occur in plasma and blood and was markedly attenuated in plasma from individuals deficient in any of the intrinsic pathway components (see, Ewald, G. A. et al. (1995) Circulation 91: 28-36).

Individuals who have had an acute MI were found to have elevated levels of activated PK and thrombin (see, Hoffmeister, H. M., et al. (1998) Circulation 98: 2527-33.

DX-88 reduced brain edema, infarct volume and neurological deficits in an animal model of ischemic stroke (see, Storini, C. et al. (2006) J. Pharm. Exp. Ther. 318: 849-854). C1-INH reduced infarct size in a mouse model of MCAO. (see, De Simoni, M. G. et al. (2004) Am. J. Pathol. 164: 1857-1863; and Akita, N. et al. (2003) Neurosurgery 52: 395-400). B2 receptor antagonists were found to reduce the infarct volume, brain swelling and neutrophil accumulation and were neuroprotective in an MCAO animal model (see, Zausinger, S. et al. (2003) Acta Neurochir. Suppl. 86: 205-207; Lumenta, D. B. et al. (2006) Brain Res. 1069: 227-234; Ding-Zhou, L. et al. (2003) Br. J. Pharmacol. 139: 1539-1547).

Regarding blood loss during cardiopulmonary bypass, it has been found that the contact system is activated during CABG (see, Wachtfogel, Y. T. (1989) Blood 73: 468) and activation of the contact system during CPB results in up to a 20-fold increase in plasma bradykinin (see, Cugno, M. et al. (2006) Chest 120: 1776-1782; and Campbell, D. J. et al. (2001) Am. J. Physiol. Reg. Integr. Comp. Physiol. 281: 1059-1070). Dyax reports that DX-88 reduced the volume of blood required for transfusion (see, www.dyax.com).

PK inhibitors, P8720 and PKSI-527 have also been found to reduce joint swelling in rat models of arthritis (see, De La Cadena, R. A. et al. (1995) FASEB J. 9: 446-452; Fujimori, Y. (1993) Agents Action 39: 42-48). It has also been found that inflammation in animal models of arthritis was accompanied by activation of the contact system (see, Blais, C. Jr. et al. (1997) Arthritis Rheum. 40: 1327-1333).

Additionally, plasma kallikrein inhibitor P8720 has been found to reduce inflammation in an acute and chronic rat model of IBD. (Stadnicki, A. et al. (1998) 12: 325-333; Stadnicki, A. et al. (1996) Dig. Dis. Sci. 41: 912-920; and De La Cadena, R. A., et al. (1995) FASEB J. 9: 446-452). The contact system is activated during acute and chronic intestinal inflammation (see, Sartor, R. B. et al. (1996) Gastroenterology 110: 1467-1481). It has been found that B2 receptor antagonist, an antibody to high molecular weight kininogen or reduction in levels of kininogen reduced clinicopathology in animal models of IBD (see, Sartor, R. B. et al. (1996) Gastroenterology 110: 1467-1481; Arai, Y. et al. (1999) Dig. Dis. Sci. 44: 845-851; and Keith, J. C. et al. (2005) Arthritis Res. Therapy 7: R769-R776).

H-D-Pro-Phe-Arg-CMK, an inhibitor of PK and FXII, and a physiological inhibitor (C1-INH) has been found to reduce vascular permeability in multiple organs and reduce lesions in LPS or bacterial induced sepsis in animals (Liu, D. et al. (2005) Blood 105: 2350-2355; Persson, K. et al. (2000) J. Exp. Med. 192: 1415-1424). Clinical improvement was observed in sepsis patients treated with C1-INH (see, Zeerleder, S. et al. (2003) Clin. Diagnost. Lab. Immunol. 10: 529-535; Caliezi, C., et al. (2002) Crit. Care Med. 30: 1722-8; and Marx, G. et al. (1999) Intensive Care Med. 25: 1017-20). Fatal cases of septicemia are found to have a higher degree of contact activation (see, Martinez-Brotons, F. et al. (1987) Thromb. Haemost. 58: 709-713; and Kalter, E. S. et al. (1985) J. Infect. Dis. 151: 1019-1027).

It has also been found that prePK levels are higher in diabetics, especially those with proliferative retinopathy, and correlate with fructosamine levels (Gao, B.-B., et al. (2007) Nature Med. 13: 181-188; and Kedzierska, K. et al. (2005) Archives Med. Res. 36: 539-543). PrePk is also found to be elevated in diabetics and is highest in those with a sensomotor neuropathy (see, Christie, M. et al. (1984) Thromb. Haemostas. (Stuttgart) 52: 221-223). PrePK levels are elevated in diabetics and are associated with increased blood pressure. PrePK levels independently correlate with the albumin excretion rate and are elevated in diabetics with macroalbuminuria suggesting prePK may be a marker for progressive nephropathy (see, Jaffa, A. A. et al. (2003) Diabetes 52: 1215-1221). B1 receptor antagonists have been found to decrease plasma leakage in a rats treated with streptozotocin (Lawson, S. R. et al. (2005) Eur. J. Pharmacol. 514: 69-78). B1 receptor antagonists can also prevent streptozotocin-treated mice from developing hyperglycemia and renal dysfunction (see, Zuccollo, A. et al. (1996) Can. J. Physiol. Pharmacol. 74: 586-589).

The present invention also represents a new paradigm for ischemic stroke treatment. Current treatments are severely limited. Traditionally, acute ischemic stroke is treated using a tissue plasminogen activator (tPA). This drug can prevent some of the adverse impacts associated with stroke but only if it is administered intravenously within the first three hours of the event and only if there is no bleeding in the brain. With such a small therapeutic window, only a small percentage of stroke patients (~3%) receive effective treatment. In recent years, stroke research has focused on developing neuroprotective agents, compounds that may make the brain more resistant to damage from stroke. The compounds of the present invention have the ability to halt the ischemic cascade.

Treatment methods provided herein include, in general, administration to a patient an effective amount of one or more compounds provided herein, e.g., orally, nasally or parenterally. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the invention are preferably administered to a patient (e.g., a human) orally. The effective amount may be an amount sufficient to modulate the PK receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit the PK receptor in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

The compounds of the present invention can be administered as frequently as necessary, including hourly, daily, weekly or monthly. Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

The compounds of formula I or II can also be administered in combination with the additional therapeutic agents or diagnostic agents.

VI. Examples

The following abbreviations are used in the Examples and throughout the description of the invention.
HOBt: N-hydroxybenzotriazole
DMSO: Dimethylsulfoxide
AmBZ: Amidinobenzylamine
DCM: Dichloromethane
DIPEA: Diisopropylethylamine Example 1

Synthesis of PK-specific Inhibitors

Synthesis of the compounds of this invention were carried out by the formation of a single amide bond between commercially available carboxylic acids (obtained from either ASDI, Inc., or Enamine, Inc., Kiev, Ukraine) and 4-amidinobenzylamine (4-AmBz, obtained from Astatech, Inc., Bristol, Pa.), using PS-Carbodiimide (obtained from Biotage, Inc., Charlottesville, Va.), and synthesis protocols supplied by Biotage (see Drawings, FIG. 1). For each synthesis, 100 μmol of PS-Carbodiimide is mixed with a separate carboxylic acid (75 μmol), 4-AmBz.2HCl (75 μmol), N-hydroxybenzotriazole (HOBt; 75 μmol) and diisopropylethylamine (DIPEA; 75 μmol), in 4 ml of 40% dimethylsulfoxide (DMSO)/60% dichloromethane (DCM), in a fitted, stoppered polypropylene reaction vessel, and mixed on a Adams Nutator for 48-72 h at room temperature. The product is obtained by filtration, followed by removal of the DCM by evaporation. Greater than 95% coupling of the carboxylic acid to the 4-AmBz takes place under these conditions, as determined by measuring the residual amount of uncoupled 4-AmBZ left by quantitation of its free amine functionality with ninhydrin. The compounds of the present invention are then purified using a Waters WCX cartridge. Approx 50 μmols of compound are applied to a 250 mg Waters WCX cartridge (pre-washed with 5 ml each of MeOH then water) in 4 ml of 50% DMSO-50% water. The cartridge is then washed with 20 ml of 5% MeOH-95% water, followed by 5 ml of MeOH. The column is then eluted with 10 ml of 5% HCOOH-95% MeOH. The compound is obtained in >95% purity following evaporation of the solvent in a Savant SpeedVac. Product integrity is determined by an analytical LC-MS/MS determination of mass of the product using a Applied Biosystems/MDS SCIEX Q-STAR mass spectrometer, following separation on a Shimadzu VP HPLC system.

Certain compounds prepared and purified using this procedure are listed in Tables 1 and 2.

Example 2

Inhibition Studies of PK Inhibitors

Human plasma kallikrein (PK) was obtained from Haemtech Technologies (Essex Junction, Vt.). The enzymatic activity of PK was assayed using the synthetic peptide substrate H-D-Pro-Phe-Arg-pNA (Bachem, Inc., Switzerland) with the cleavage of the substrate by the enzyme resulting in an increase in $A_{405}$, measured using a Molecular Devices $V_{max}$ Kinetic Microplate Reader. The uninhibited (control) activity of PK was determined by adding 190 µl of PK solution (1 nM in 0.05 M HEPES, pH 7.5, 0.01% Triton X-100) to 10 µl of H-D-Pro-Phe-Arg-pNA (2 mM in DMSO) in individual microtiter plate wells, mixed immediately by shaking, and the rate of increase in A405 determined over 120-180 sec. In parallel, compounds of the present invention were mixed in separate wells with the synthetic substrate to attain final concentrations of between 0.01-10 µM in the final 200 µl reaction mixture, and the reaction initiated by the addition of 190 µl of the PK solution. A diminished rate of cleavage in the presence of a compound denotes inhibition of PK activity, and the apparent inhibition constant of the interaction can be determined by using the following equation—

$$K_{i,app} = [I]/(PK_{Control}/PK_I - 1)$$

where [I]=concentration of inhibitory compound, $PK_{Control}$=rate of substrate cleavage by uninhibited PK, $PK_I$=rate of substrate cleavage by PK in the presence of inhibitory compound.

The corrected $K_i$ of the interaction can be obtained as follows from the calculated $K_{i,app}$—

$$K_i = K_{i,app}/([S]/K_m + 1)$$

Where [S]=concentration of synthetic substrate, and $K_m$=Michaelis constant of synthetic substrate for PK, in this case determined experimentally to be 0.15 mM under these conditions.

Table 4 lists the inhibition constants for certain compounds having the following formula:

TABLE 4

Inhibition constants

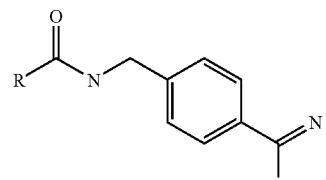

| | 1 | 2 | 3 | 4 |
|---|---|---|---|---|
| R* | 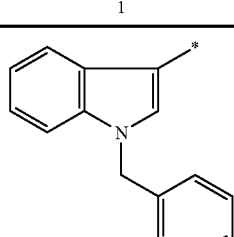 | 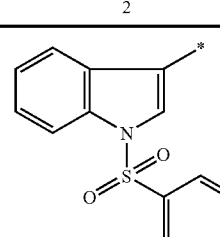 | 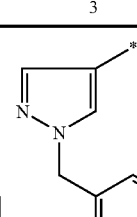 | 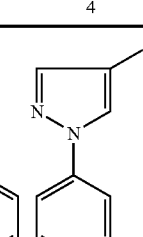 |
| Ki, µM | 0.08 | 0.03 | 0.15 | 1 |

*= point of attachment to 4-amidinobenzylamide moiety

Inhibitory Effect of ASP-440 and ASP-465

The inhibitory effect of ASP-440 and ASP-465 towards purified human PK as well as other enzymes in both the intrinsic and extrinsic pathways of coagulation is shown in Table 5. The numbers are expressed as $K_i$ values (µM), obtained after determining the extent of inhibition, if any, of a given enzyme's amidolytic activity for a suitable synthetic substrate (S-2302 or Chromozym TH) in the presence of increasing amounts of either ASP-440 or ASP-465. The highest concentration of either compound tested was 10 µM. The results shown in Table 5 demonstrate that ASP-440 and ASP-465 are potent inhibitors of PK, with ASP-465 being 3-fold more potent than ASP-440. In addition, ASP-440 shows >100-fold selectivity against all of the other enzymes tested, and ASP-440 shows >300-fold selectivity against all of the other enzymes tested.

TABLE 5

Specificity Profile of PK Inhibitors ($K_i$ values)

| | PK | FXa | FXIa | FXIIa | Thrombin | Plasmin |
|---|---|---|---|---|---|---|
| ASP-440 | 0.09 µM | >10 µM | >10 µM | >10 µM | >10 µM | >10 µM |
| ASP-465 | 0.03 µM | >10 µM | >10 µM | >10 µM | >10 µM | >10 µM |

Example 3

Determination of Anticoagulation Activity of PK Inhibitors

In order to determine the role of PK for thrombin generation, fibrin cleavage, and consequent fibrin clot formation upon activation of the intrinsic pathway, commercially available Actin FS reagent (Dade-Behring) was used to initiate contact activation of the intrinsic pathway. Human plasma (50 µl) was mixed with Actin FS (50 µl) supplemented with 15 mM $CaCl_2$ in individual wells of a clear polystyrene 96-well microplate, and the time course and extent of fibrin cleavage and clot formation was determined by monitoring $A_{405}$ as a function of time in a kinetic microplate reader (Molecular Devices $V_{max}$). Clot formation resulted in turbidity registering as an apparent increase in $A_{405}$. This was verified visually at the end of each experiment. The time to coagulation was defined as the time to reach ½ maximal $\Delta A_{405}$. All data points are plotted as mean±SD of triplicate determinations (n=3).

Figure 2:
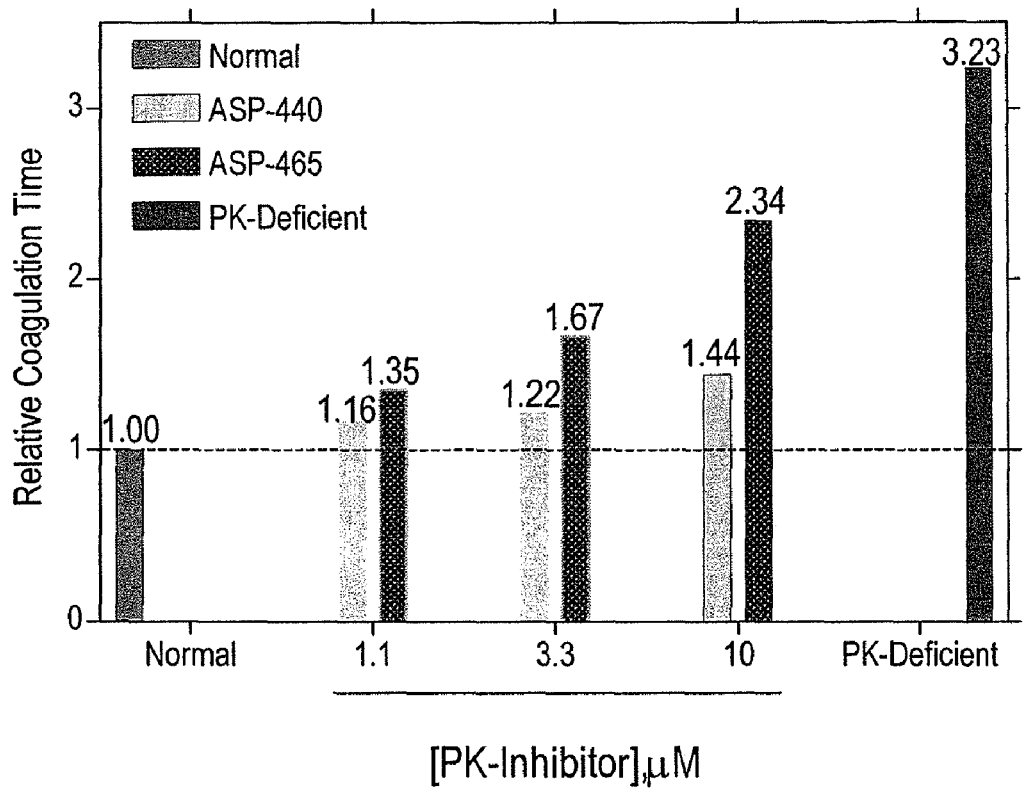
FIG. 2 illustrates the dose-dependency of prolonged coagulation times of normal plasma with the addition of ASP-440 or ASP-465 at various concentrations, and the clotting time of PK-deficient plasma.

Under these conditions, PK-deficient plasma (PK levels<1% of normal, obtained from George King Biomedical, Overland Park, Kans.) coagulated following Actin FS addition with a clotting time>3-fold higher than that seen with normal plasma (FIG. 1). This therefore marks the maximum amount of inhibition of contact activated coagulation in human plasma that can be achieved with PK inhibition. The ability of the compounds of the present invention to inhibit contact activated coagulation can then be measured by adding the compound to the plasma-Actin FS mixture at various concentrations (0.1-10 µM) and determining the coagulation time, and ranking the compounds by the extent of inhibition of contact activated coagulation achieved at 10 µM. For example, addition of either ASP-440 or ASP-465 to normal plasma at 1.1, 3.3 or 10 µM, dose-dependently prolonged time to coagulation by 16-134%, with ASP-465 prolonging time to coagulation more at each concentration than ASP-440 (FIG. 2).

Example 4

Thrombogenic Effect of Plasmin is Mediated Via the Intrinsic Pathway and Requires Plasma Kallikrein (PK)

In the clotting paradigm utilized in Example 3, plasma is mixed 1:1 with commercially formulated Actin FS. Thus, 50% (v/v) Actin FS is the maximum amount of activator that can be added while maintaining the amount of plasma constant at 50% of the incubation mixture. Since the clotting time in normal plasma is dependent on the amount of Actin FS present in the incubation mixture, these conditions would by definition lead to the shortest time to coagulation mediated by the intrinsic pathway in this paradigm. Lowering the amount of contact activator leads to a decrease in the amount of PK activated, thus reducing the amount of thrombin generated and slowing the time to coagulation (data not shown). Therefore, in order to determine whether addition of exogenous plasmin (mimicking a fibrinolytic setting) can shorten time to coagulation, the amount of Actin FS reagent added to the plasma (kept constant at 50% of the final incubation mixture) was lowered so as to attain 6.25% (final v/v). This level significantly increases the control time to coagulation, and thus provides an experimental window for measuring a shorter coagulation time.

Figure 3:
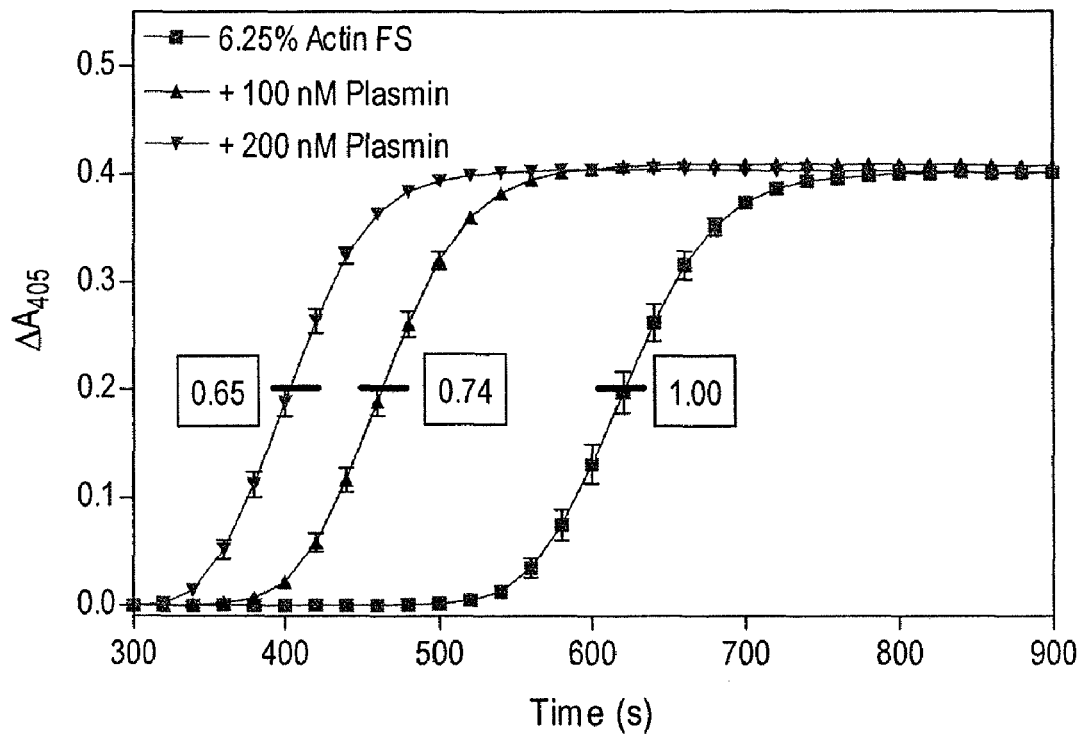
FIG. 3 illustrates the addition of exogenous plasmin at 100 or 200 nM to the 50% plasma- 6.25% Actin FS incubation mixture resulted in a dose-dependent shortening of the time to coagulation, for example, relative coagulation time decreases from 1.00 to 0.74 to 0.65.

Addition of exogenous plasmin at 100 or 200 nM to the 50% plasma-6.25% Actin FS incubation mixture resulted in a dose-dependent shortening of the time to coagulation (relative coagulation time decreases from 1.00 to 0.74 to 0.65, see, FIG. 3). Plasmin at 200 nM added to plasma in the absence of any Actin FS demonstrated a very slow relative time to coagulation of 4.0 (data not shown), indicating that the presence of the contact activator was necessary for plasmin to have any significant thrombogenic effect. This provides direct evidence that plasmin can have a thrombogenic effect when added to plasma in the presence of a small amount of contact activator.

Figure 4:
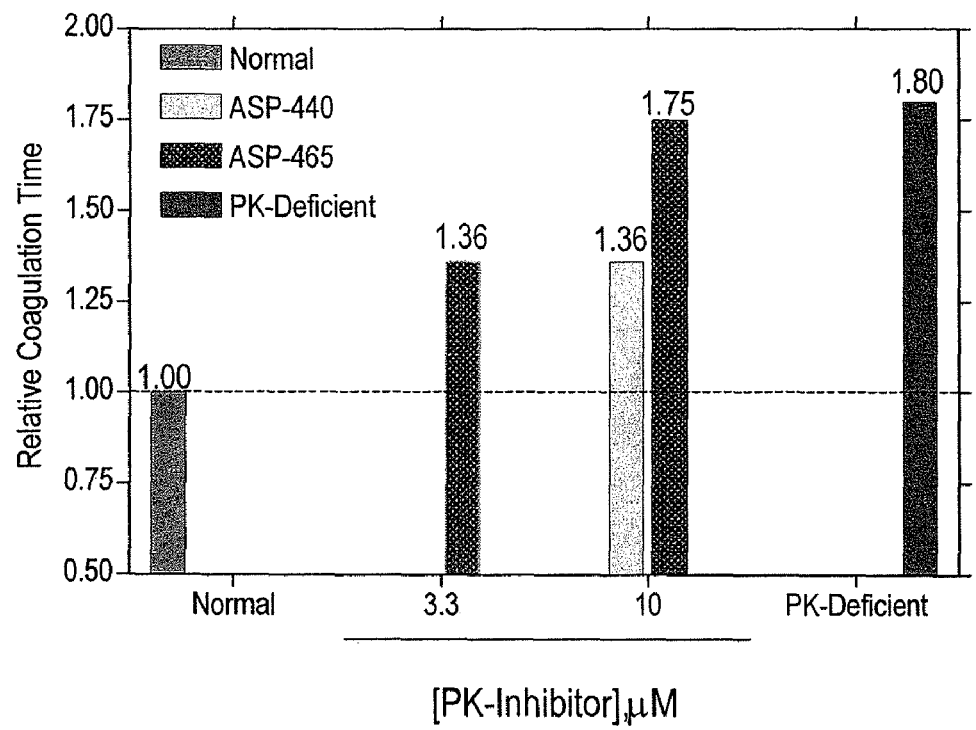
FIG. 4 illustrates that PK-specific inhibitors can effectively inhibit the plasmin-mediated thrombogenic effect in plasma and the presence of PK is required for plasmin to exert its thrombogenic effect in plasma.

Addition of 200 nM plasmin to PK-deficient plasma under otherwise identical experimental conditions resulted in a time to coagulation 80% greater than that seen with normal plasma (FIG. 4), demonstrating that the presence of PK is required for plasmin to exert its thrombogenic effect in plasma. Addition of ASP-440 (10 µM) or ASP-465 (3.3 or 10 µM) to normal plasma in the presence of 200 nM plasmin (FIG. 4) prolongs time to coagulation by 36% (ASP-440) or by 36-75% (ASP-465). Thus, PK-specific inhibitors can effectively inhibit the plasmin-mediated thrombogenic effect in plasma, with ASP-465 showing the same degree of prolongation at 3.3 µM as does ASP-440 at 10 µM. As demonstrated in Table 2, the in vitro $K_i$ of ASP-465 towards PK is exactly 3-fold lower than that of ASP-440—in agreement with its observed 3-fold greater potency towards inhibiting plasmin-activated coagulation. Importantly, ASP-465 at 10 µM (FIG. 4) almost completely blocks the plasmin-induced shortening of time to coagulation that is attributable to PK—demonstrating the utility of a small molecule PK inhibitor in this clinically important paradigm.

Example 5

Figure 5:
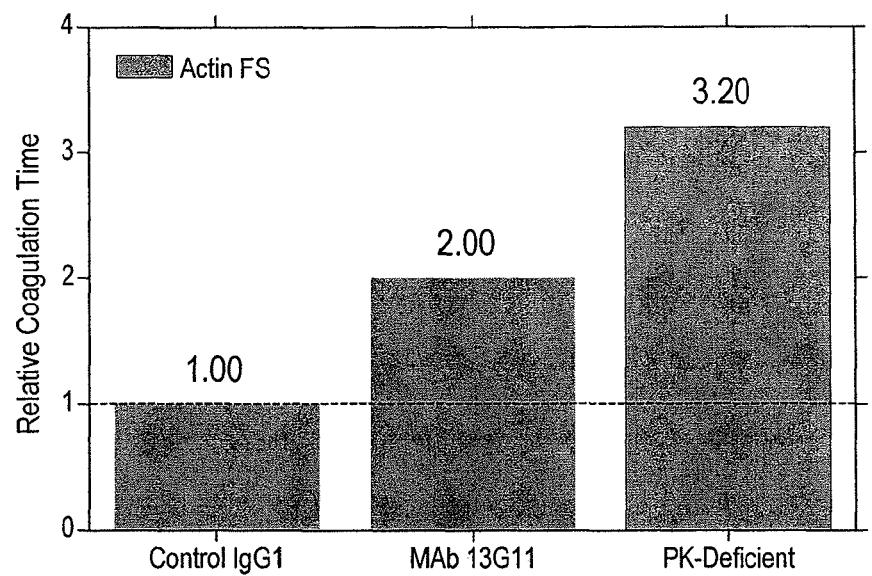
FIG. 5 illustrates that monoclonal antibody (MAB) 13G11 prolongs the coagulation time by 100% when plasma is activated using 50% Actin FS.
Figure 6:
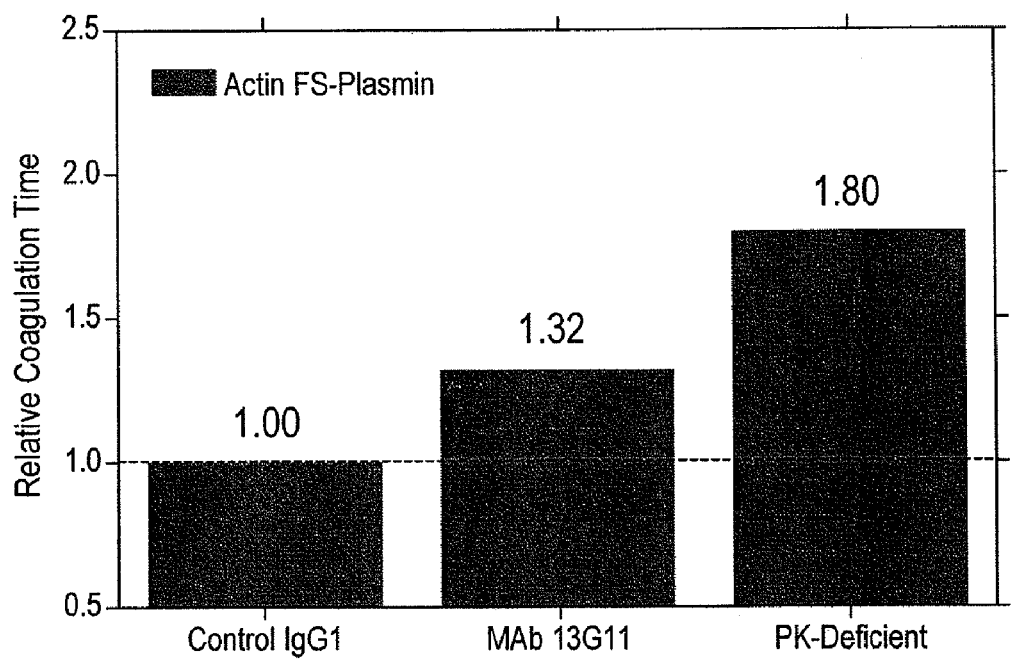
FIG. 6 illustrates that MAB 13G11 prolongs the coagulation time by 32% when plasma is activated using 200 nM plasmin and 6.25% Actin FS.

A Specific MAb to PK Inhibits Contact-Activated Coagulation and Plasmin-Activated Thrombogenesis The previous examples have demonstrated that PK is critical for contact-activated coagulation via the intrinsic pathway, as well as for plasmin-activated thrombogenesis. The role for PK was established by evaluating deficiencies in PK, as well as by using two specific inhibitors of the enzymes. In order to determine whether blocking PK via a specific monoclonal antibody (MAb) would also be effective in inhibiting coagulation in either of the two paradigms described here, and thus provide additional validation for the invention, MAb 13G11, which has been previously characterized as being specific for PK (Veloso et al, (1987) *Blood,* 70, 1053-1062), was tested in each of the coagulation paradigms described in Examples 2 and 3. MAb 13G11 (obtained from GeneTex, San Antonio, Tex.) was added at a final concentration of 0.036 mg/ml in the 50% plasma-50% activator mix in each paradigm. This calculates to an approximately 2-fold molar excess over the amount of PK that would be present in the plasma-activator mixture, based on the literature reference of Veloso et al, (1987), *Blood,* 70, 1053-1062. Control samples were treated with 0.036 mg/ml of an isotype-matched control IgG1 (also obtained from GeneTex). When plasma was activated using 50% Actin FS (FIG. 5), MAb 13G11 prolonged time to coagulation by 100% (45% of the maximal effect obtained with PK-deficient plasma), and, when plasma was activated using 200 nM plasmin+6.25% Actin FS (FIG. 6), prolonged time to coagulation by 32% (40% of the maximal effect obtained with PK-deficient plasma). Therefore, a highly specific MAb to PK is equally effective in blocking coagulation mediated by the intrinsic pathway triggered by contact activation (±plasmin), and at 2-fold molar excess over PK, is as efficacious as is the highly specific PK inhibitor ASP-440 at 10 μM.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A method of treating a disease or condition selected from the group consisting of retinopathy, proliferative retinopathy, neuropathy, increased blood pressure, brain edema, increased albumin excretion, macroalbuminuria and nephropathy, said method comprising administering to a subject in need thereof a pharmaceutically effective amount of a compound having formula (I):

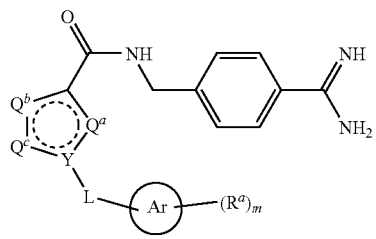

wherein
Ar is a bond or an aromatic ring selected from the group consisting of benzene, pyridine and pyrimidine;
the subscript m is an integer of from 0 to 5;
each $R^a$ is independently selected from the group consisting of cycloalkyl, $(C_1-C_8)$haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —NR$^1$—OR$^1$, —N=C=O, —N=C=S, —Si(R$^1$)$_3$, —NH—NHR$^1$, —NHC(O)NHNH$_2$, NO, —N=C=NR$^1$ and —S—CN, wherein each R$^1$ is independently alkyl;
L is a linking group selected from the group consisting of a bond, CH$_2$ and SO$_2$;
$Q^a$, $Q^b$, and $Q^c$ are each members independently selected from the group consisting of N, S, O and C(R$^q$) wherein each R$^q$ is independently selected from the group consisting of H, C$_{1-8}$ alkyl, halo and phenyl, and the ring having $Q^a$, $Q^b$, $Q^c$ and Y as ring vertices is a five-membered ring having two double bonds;
Y is a member selected from the group consisting of C and N;
when Ar is a bond, m is 1;
when Ar is an aromatic ring, m is an integer of from 0-5; and pharmaceutically acceptable salts thereof.

2. A method of claim 1, wherein said disease or condition is proliferative retinopathy.

3. A method of claim 1, wherein said disease or condition is increased blood pressure.

4. A method of claim 1, wherein said compound is selected from the group consisting of:

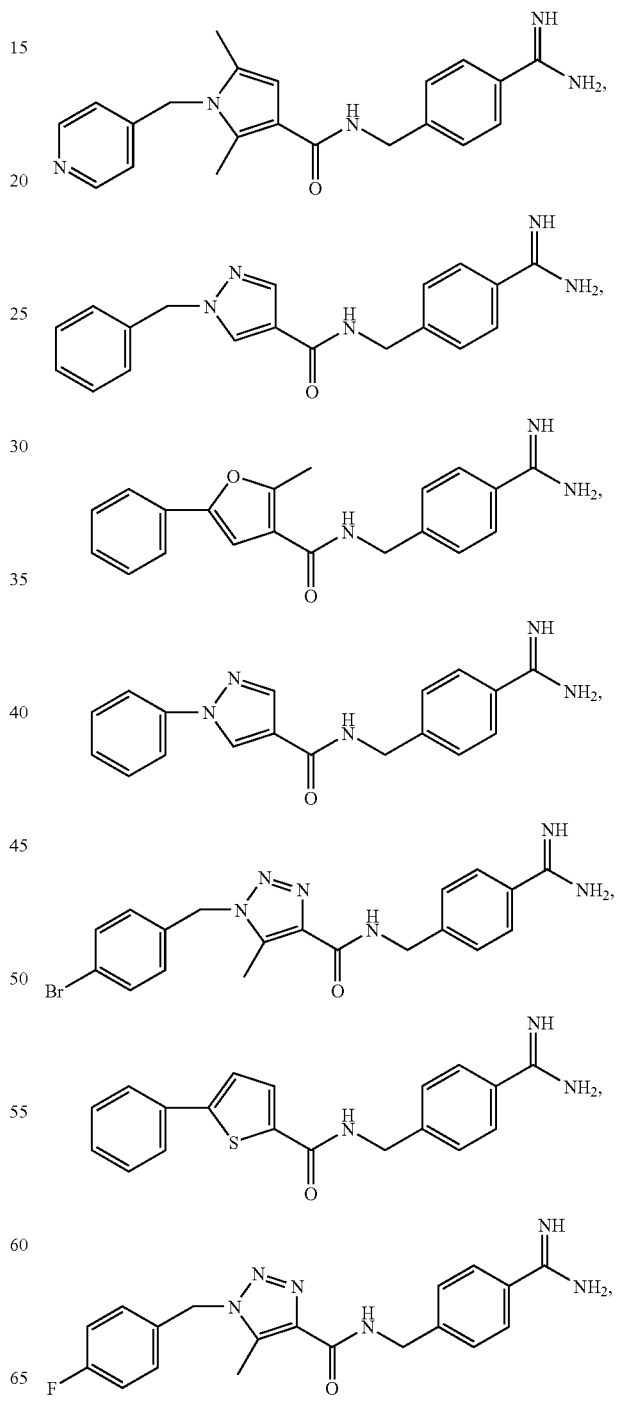

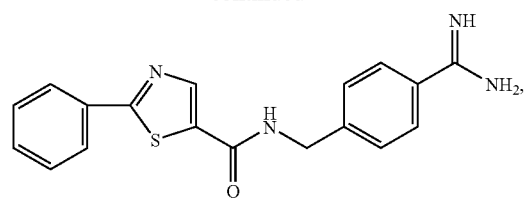

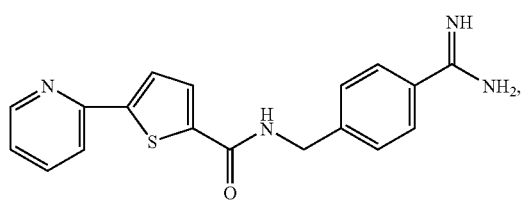

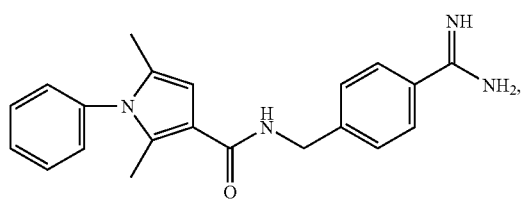

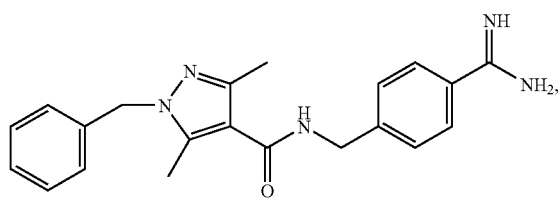

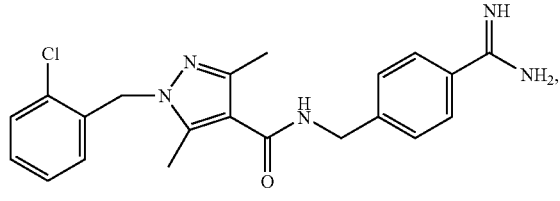

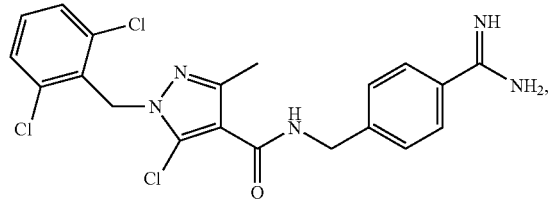

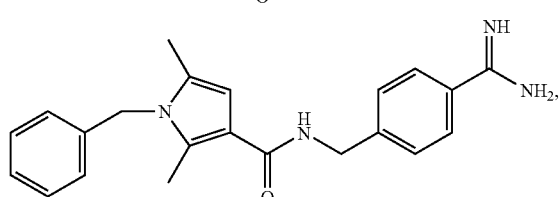

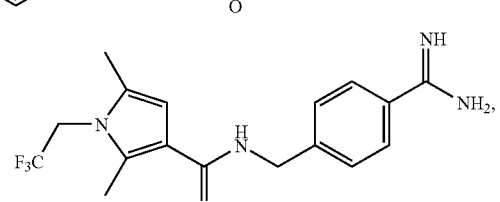

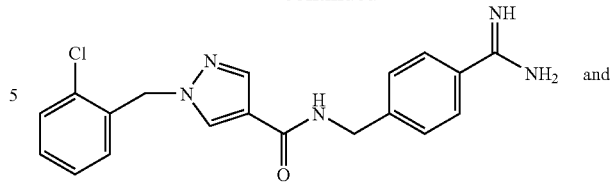

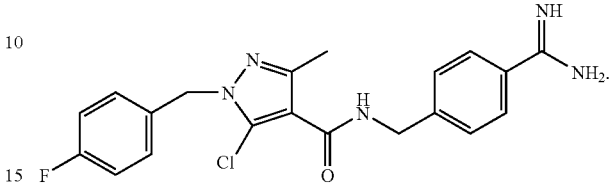

and

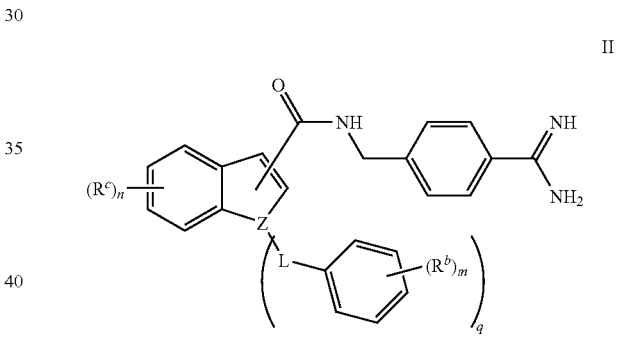

5. A method of treating a disease or condition selected from the group consisting of stroke, inflammation, pain, acute myocardial infarction, deep vein thrombosis (DVT), post fibrinolytic treatment conditions, angina, angioedema, sepsis, arthritis, blood loss during cardiopulmonary bypass, inflammatory bowel disease, diabetes, retinopathy, proliferative retinopathy, neuropathy, increased blood pressure, brain edema, increased albumin excretion, macroalbuminuria and nephropathy, said method comprising administering to a subject in need thereof a pharmaceutically effective amount of a compound having formula II:

II wherein the subscript m is an integer of from 0 to 5;
the subscript n is an integer of from 0 to 4;
the subscript q is an integer of from 0 to 1;
L is a linking group selected from the group consisting of a bond, $CH_2$ and $SO_2$;
each of $R^b$ and $R^c$ is independently selected from the group consisting of cycloalkyl, $(C_1$-$C_8)$haloalkyl, halogen, —OH, —$OR^2$, —$OSi(R^2)_3$, —$OC(O)O$—$R^2$, —$OC(O)R^2$, —$OC(O)NHR^2$, —$OC(O)N(R^2)_2$, —SH, —$SR^2$, —$S(O)R^2$, —$S(O)_2R^2$, —$SO_2NH_2$, —$S(O)_2NHR^2$, —$S(O)_2N(R^2)_2$, —$NHS(O)_2R^2$, —$NR^2S(O)_2R^2$, —$C(O)NH_2$, —$C(O)NHR^2$, —$C(O)N(R^2)_2$, —$C(O)R^2$, —$C(O)H$, —$C(=S)R^2$, —$NHC(O)R^2$, —$NR^2C(O)R^2$, —$NHC(O)NH_2$, —$NR^2C(O)NH_2$, —$NR^2C(O)NHR^2$, —$NHC(O)NHR^2$, —$NR^2C(O)N(R^2)_2$, —$NHC(O)N(R^2)_2$, —$CO_2H$, —$CO_2R^2$, —$NHCO_2R^2$, —$NR^2CO_2R^2$, —$R^2$, —CN, —$NO_2$, —$NH_2$, —$NHR^2$, —$N(R^2)_2$, —$NR^2S(O)NH_2$, —$NR^2S(O)_2NHR^2$, —$NH_2C(=NR^2)NH_2$, —$N=C(NH_2)NH_2$, —$C(=NR^2)NH_2$, —NH—OH, —$NR^2$—OH, —$NR^2$—$OR^2$, —N=C=O, —N=C=S, —$Si(R^2)_3$, —NH—$NHR^2$, —$NHC(O)NHNH_2$, NO, —N=C=NR² and —S—CN, wherein each $R^2$ is independently alkyl;

when q is 0, Z is a member selected from the group consisting of O, S and $NR^d$ wherein $R^d$ is H or $C_1$-$C_8$ alkyl;

when q is 1, Z is N; and pharmaceutically acceptable salts thereof.

6. A method of claim 5, wherein said disease or condition is proliferative retinopathy or increased blood pressure.

7. A method of claim 5, wherein said disease or condition is proliferative retinopathy.

* * * * *

UNITED STATES PATENT AND TRADEMARK OFFICE
CERTIFICATE OF CORRECTION

PATENT NO. : 7,977,380 B2  Page 1 of 1
APPLICATION NO. : 12/623326
DATED : July 12, 2011
INVENTOR(S) : Sinha et al.

It is certified that error appears in the above-identified patent and that said Letters Patent is hereby corrected as shown below:

On the Face Sheet:
First column, item (73): please delete "Pharmaceticals" and insert --Pharmaceuticals--.

Signed and Sealed this
First Day of November, 2011

David J. Kappos
*Director of the United States Patent and Trademark Office*